(12) United States Patent
Frering

(10) Patent No.: US 7,282,023 B2
(45) Date of Patent: Oct. 16, 2007

(54) METHOD AND DEVICE FOR CONTROLLING THE INFLATION OF AN INFLATABLE PROSTHETIC ENVELOPE

(75) Inventor: Vincent Frering, Lyons (FR)

(73) Assignee: Magnetic Developpement Medical, Limonest (FR)

( * ) Notice: Subject to any disclaimer, the term of this patent is extended or adjusted under 35 U.S.C. 154(b) by 582 days.

(21) Appl. No.: 10/363,733

(22) PCT Filed: Sep. 7, 2001

(86) PCT No.: PCT/FR01/02777

§ 371 (c)(1),
(2), (4) Date: Mar. 7, 2003

(87) PCT Pub. No.: WO02/19953

PCT Pub. Date: Mar. 14, 2002

(65) Prior Publication Data

US 2004/0102677 A1    May 27, 2004

(30) Foreign Application Priority Data

Sep. 11, 2000   (FR) .................................. 00 11819

(51) Int. Cl.
*A61F 2/02*    (2006.01)

(52) U.S. Cl. ...................................................... 600/31

(58) Field of Classification Search ............ 600/38–41, 600/37, 29–31; 128/897, 898
See application file for complete search history.

(56) References Cited

U.S. PATENT DOCUMENTS

| 4,167,952 | A | * | 9/1979 | Reinicke ...................... 137/493 |
| 4,383,525 | A | * | 5/1983 | Scott et al. .................... 600/40 |
| 4,407,278 | A | * | 10/1983 | Burton et al. ................. 600/40 |
| 4,437,457 | A |   | 3/1984 | Trick et al. |
| 4,587,954 | A | * | 5/1986 | Haber .......................... 600/31 |
| 4,724,830 | A | * | 2/1988 | Fischell ....................... 600/40 |
| 4,917,110 | A | * | 4/1990 | Trick ........................... 600/40 |
| 4,994,020 | A | * | 2/1991 | Polyak ......................... 600/31 |
| 5,803,897 | A | * | 9/1998 | Mooreville et al. ........... 600/40 |

FOREIGN PATENT DOCUMENTS

| EP | 0626154 | 11/1994 |
| WO | 0009049 | 2/2000 |

* cited by examiner

*Primary Examiner*—Samuel G Gilbert
(74) *Attorney, Agent, or Firm*—Dennison, Schultz & MacDonald

(57) ABSTRACT

A method and device for controlling the inflation of a prosthesis, particularly applicable to gastric implants. A liquid-containing bag is connected to a unit defining a transfer circuit under the control of the shutter and connected to an inflatable envelope, where the shutter is constituted by a non-return check valve closable and openable magnetically by remote control.

14 Claims, 4 Drawing Sheets

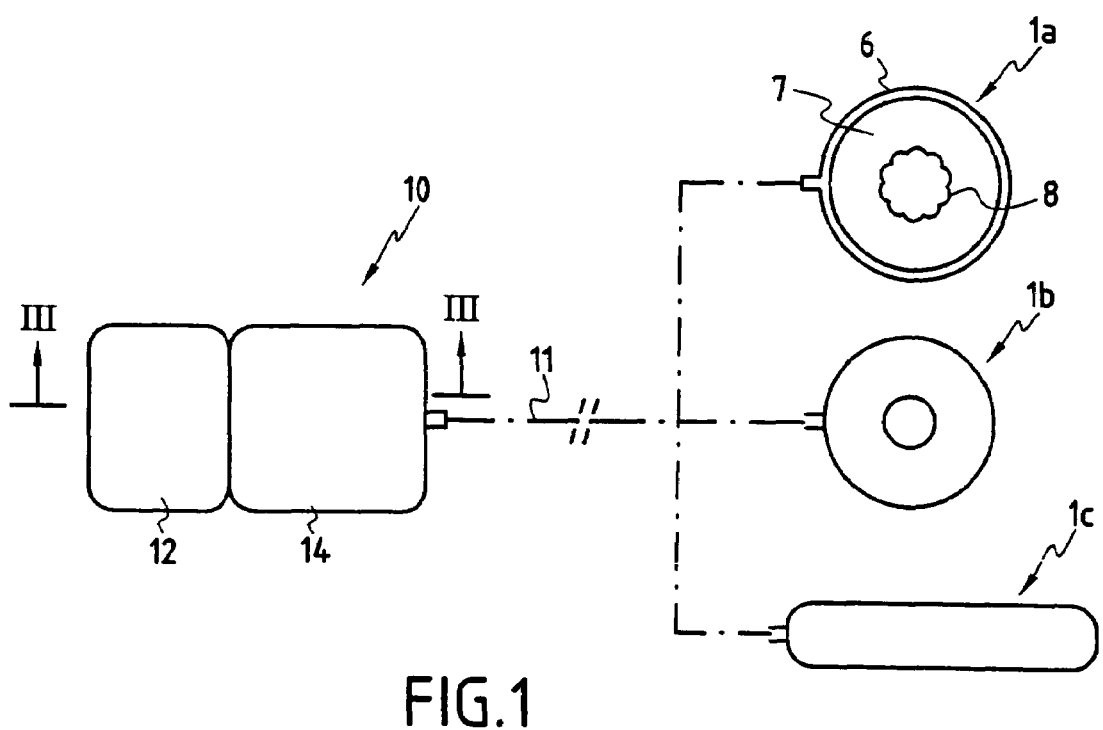
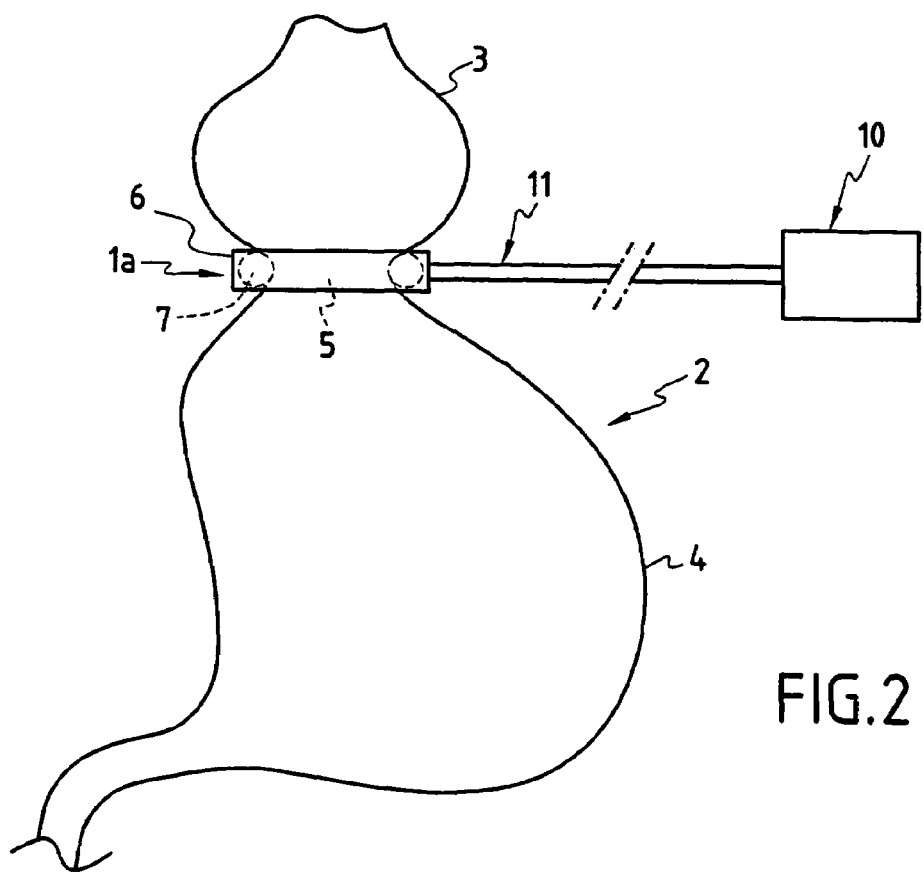
FIG.1
FIG.2

METHOD AND DEVICE FOR CONTROLLING THE INFLATION OF AN INFLATABLE PROSTHETIC ENVELOPE

This application is a filing under 35 USC 371 of PCT/FR01/02777, filed Sep. 7, 2001.

The present invention relates to the technical field of prostheses for the human body, and it relates more particularly to prostheses which possess as active members one or more reversibly-deformable elements.

More specifically, the invention relates to prostheses of the type including an inflatable and elastically-deformable envelope and having the function of taking the place of a failed human organ, or indeed of reversibly modifying the behavior of a human organ that has not completely failed in its function, but for which it is essential, necessary, useful, or even preferable to alter its functional capacity, at least temporarily.

Amongst possible applications, mention can be made in non-limiting manner of prosthetic envelopes performing a sphincter function, prosthetic envelopes performing a penile function, and prosthetic envelopes having a gastric implant function for defining a pocket or cavity of relatively small volume in the top portion of the stomach and in communication with the remainder of the stomach via a channel or duct that is calibrated by means of a prosthetic envelope or a gastric implant.

The envelopes implemented for the above purposes present the characteristic of being constituted at least in part by an elastically deformable wall that can be inflated or deflated at will by admitting or removing an appropriate fluid, generally a liquid, and more specifically a liquid of the physiological serum type.

For proper operation, such prosthetic envelopes require skill in monitoring or controlling inflation that may be necessary several times a day, or only occasionally, depending on the application.

Nevertheless, in all cases, it is appropriate to have technical means available suitable for performing such a function with all of the requirements that can be associated therewith, specifically: discretion, ease of use, reliability, and comfort, whether for the patient fitted with the prosthesis or for the practitioner taking functional control of the prosthetic envelope that has been implanted.

Although the solutions put forward in the prior art take account of such a general objective, it can be considered that the technical means on offer are not capable of fully satisfying the requirements encountered, nor of making genuine total, practical, easy, and comfortable implantation possible. The need to satisfy this general problem is felt in particular for reasons of comfort in the context of prosthetic envelopes of sphincter or penile function, and it is also important to consider the requirements for safety that must also be satisfied in the context of a gastric implant. As a general rule, such a prosthetic envelope fitted around the bag constituting the stomach is connected to a unit provided with a self-sealing diaphragm which can be pierced by a syringe needle or the like to enable liquid to be injected or removed in order to control deployment of the envelope whose purpose is to induce a striction effect on the stomach.

Follow-up care of implanted patients requires periodic inspection operations to be performed at least to assess that the striction induced is properly adjusted as a function of the desired results of combating alimentary obesity of the implanted patient.

That is why an inspection stage is often performed using X-rays applied by an appropriate method so as to give the practitioner a real image of the situation of the implant in order to decide whether to inject into or extract from the subcutaneously-positioned unit in order to increase or decrease the amount of striction produced.

However, practitioners undertake this kind of activity much more frequently than they perform implantation operations, and as a result they are exposed to a corresponding amount of irradiation by the X-ray apparatus implemented.

Such exposure is of a kind that can lead to unfortunate consequences on the health of practitioners who need to be protected therefrom while nevertheless inspecting implantation or adjusting the implant as they need to do periodically.

A particular object of the present invention is to satisfy these multiple requirements associated with the operation of implantable and inflatable prosthetic envelopes.

To achieve the above objects, the invention provides a method which is characterized in that it consists in:
 confining in a bag, which is deformable, a quantity of liquid that is not less than the capacity of the envelope;
 interposing, between said bag and the envelope, a non-return check valve;
 transferring a maximum quantity of liquid from the bag so as to inflate the envelope; and
 voluntarily causing the check valve to open to allow liquid that has been admitted into the envelope to return in order to deflate the envelope until it reaches the volume appropriate for the function to be performed.

The invention also provides apparatus for controlling the inflation of an implantable prosthetic envelope, such apparatus being characterized in that:
 the bag is connected to a unit defining a transfer circuit under the control of the shutter and itself connected to the envelope; and
 the shutter is constituted by a non-return check valve with magnetic remote-controlled opening.

The invention also provides an implantable and inflatable prosthesis implementing the above apparatus.

Various other characteristics appear from the following description given with reference to the accompanying drawings which show an embodiment of the invention by way of non-limiting example.

FIG. 1 is a diagrammatic view showing an embodiment of a prosthesis of the invention in the context of a variety of particular applications.

FIG. 2 is a diagrammatic elevation view showing one of the applications in greater detail.

FIG. 1 shows an inflatable prosthesis 1a, or 1b, or 1c that is implantable and that is implemented in the form of an envelope that is elastically deformable and inflatable.

Figure 3:
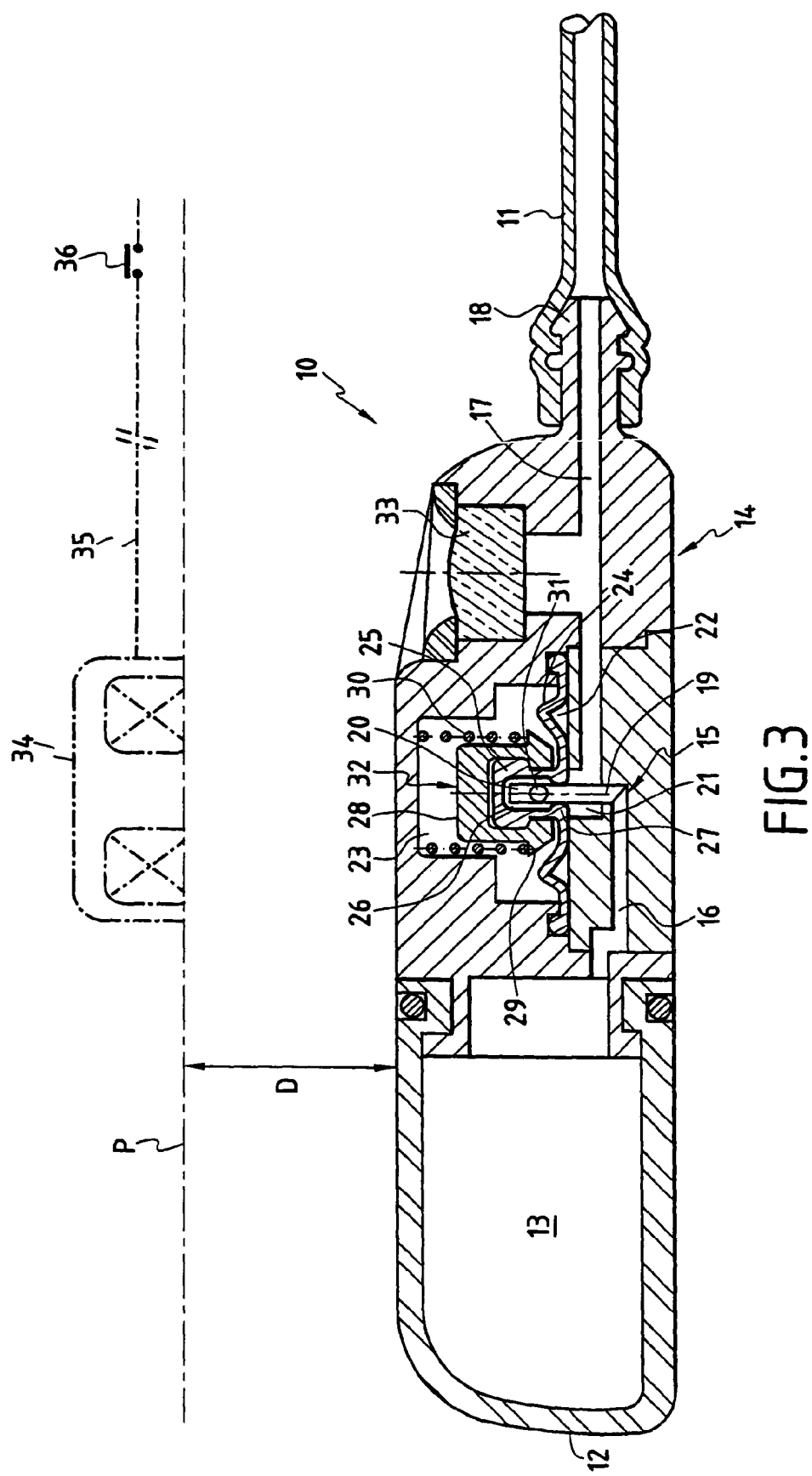
FIG. 3 is an elevation view in section on line III-III of FIG. 1 showing, on a different scale, the structure of the control apparatus.

Depending on the intended application, such an implantable prosthetic envelope may present a variety of structural shapes.

By way of example, the prosthetic envelope 1a corresponds to a gastric implant of the kind shown in FIG. 2 which is intended for being implanted in a high sub-hiatal position on a stomach 2 in such a manner as to define an artificial gastric pocket 3 which is in communication with the lower gastric pocket 4 via a communication channel 5 of through section that is controlled by the gastric implant 1a.

In order to perform the function described, the prosthetic envelope 1a comprises a belt 6 made of flexible material that is not elastically deformable which can advantageously be of the open type and possess releasable fastener means at its end portions (not shown) so as to facilitate implantation around the stomach 2.

The belt 6 is associated with an annular envelope 7 made of elastically-deformable material and occupying the inner peripheral surface of the belt 6 in such a manner that adjusting the inflation of the envelope serves to modify the through section 8 which determines the degree of striction of the communication channel 5.

The example relating to the prosthetic envelope 1a is purely illustrative, it being understood that the invention covers other structure adapted to other functions that can be envisaged.

For example, the prosthetic envelope 1b corresponds to a sphincter application, i.e. substituting a natural sphincter that has failed with an envelope such as 1b which serves to open or close the natural sphincter by being inflated or deflated as a function of requirements.

Another example is illustrated by the prosthetic envelope 1c which is implemented in the form of an elongate inflatable balloon for performing an erectile function, for example to substitute for a failed natural organ.

In order to perform the desired function, the prosthesis includes apparatus 10 for monitoring and controlling inflation of the envelope 1.

The apparatus 10 is intended to give implanted patients or practitioners the ability to control inflation of the prosthetic envelope, and for this purpose it comprises the following means which are likewise designed to be implanted, generally in a subcutaneous layer. For this purpose, the apparatus 10 described below is connected to the inflatable envelope via a transfer tube or duct 11 of length that can vary to a large extent depending on the intended application.

In FIG. 3, the apparatus 10 comprises a bag 12 made of any suitable elastically-deformable material capable of defining a tank 13 suitable for containing a quantity of liquid such as physiological serum that is not less than the quantity that can be taken in by the inflatable envelope 1a, 1b, or 1c on being inflated. In the meaning of the invention, it is particularly advantageous for the bag 12 to be made in such a manner as to possess shape memory concerning its own maximum retention capacity.

The bag 12 is associated with a control unit 14 either directly as shown in FIG. 3 or via a communication duct putting the tank 13 into communication with the internal structure of the control unit 14 which is made in such a manner as to contain an internal transfer circuit 15 possessing one branch 16 in communication with the tank 13 and another branch 17 opening out into an endpiece 18 to which the tube or duct 11 is connected.

Figure 4:
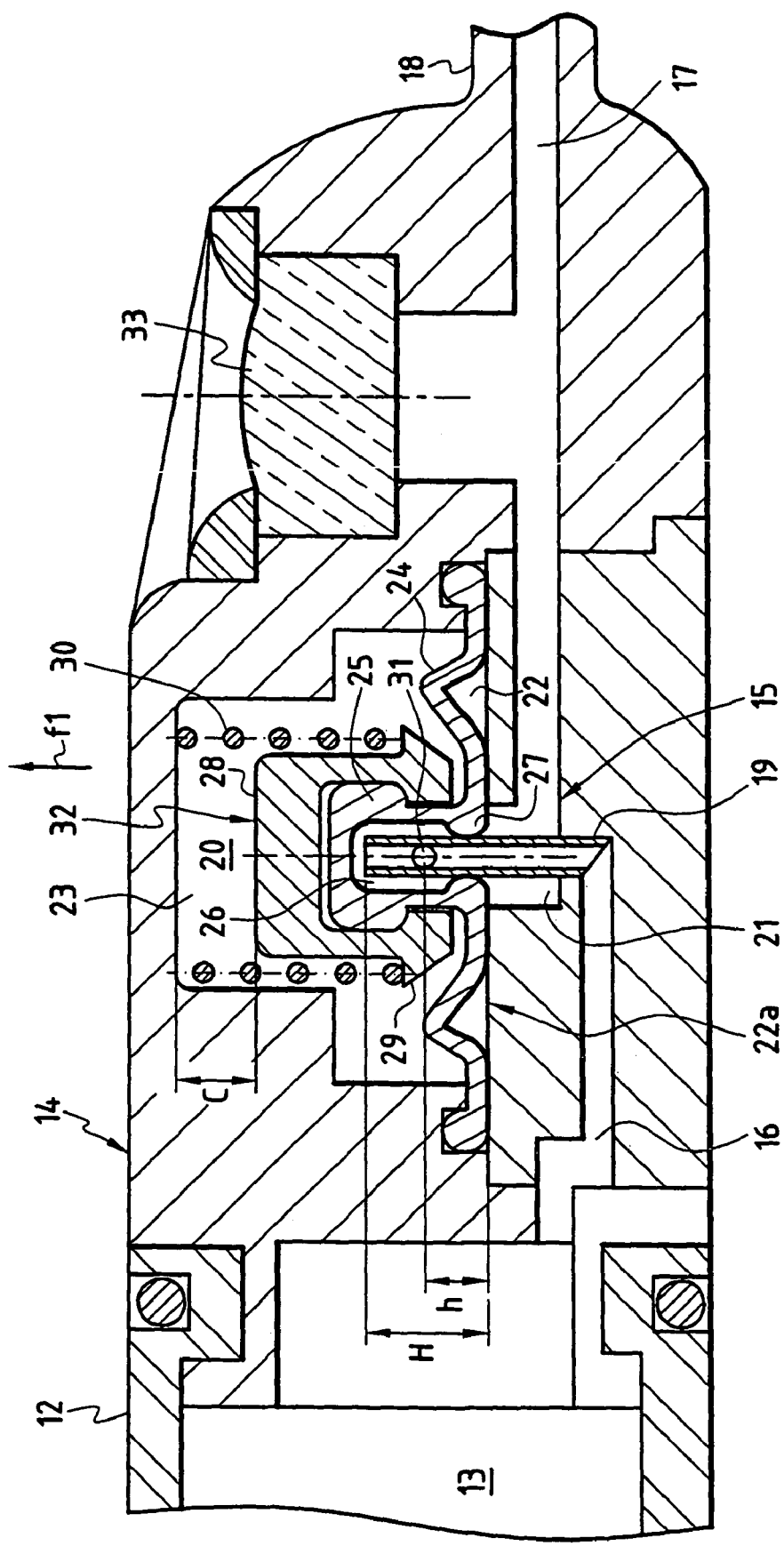
FIGS. 4 and 5 are fragmentary elevations in section on a larger scale showing functional states of the apparatus.

As shown clearly in FIG. 4, the first branch 16 is provided with a tube 19 that is open at its tip 20 and that passes axially through a prechamber 21 presented by the second branch 17 so as to open out into a chamber 22 which is provided in a cavity 23 presented by the unit 14 by means of an elastically deformable diaphragm 24. The diaphragm 24 forms a nipple 25 defining an upside-down well 26 in which the terminal portion of the tube 19 is engaged, the diaphragm being in contact therewith via a sealing gasket 27 of the lip or O-ring type. The nipple 25 carries a head 28 made of ferromagnetic material and forming a shoulder 29 at its base against which a resilient return member 30 bears, said member being placed under prestress between the shoulder 29 and the end wall of the cavity 23.

The resilient member 30 is designed to maintain the sensing member constituted by the diaphragm 24 in a position in which the chamber 22 is reduced to its minimum volume, in which the prechamber 21 is closed and in which at least one radial hole 31 presented by the tube 19 opens out into the well 26, being isolated in leaktight manner from the chamber 22 and the prechamber 21.

By construction, the assembly comprising the head 28, the nipple 25, the diaphragm 24, the tube 19, and the spring 30 constitutes a non-return check valve or shutter 32 having the special feature of being openable under control. In addition, this check valve presents the characteristic of possessing an open-to-closed stroke of length C whereas the tube 19 extends over a height H from the bearing plane $22_a$ defined by the chamber 22 for the diaphragm 24 which is greater than the stroke C. Still by construction, the radial hole 31 is placed so as to be situated relative to the plane $22_a$ at a height $\underline{h}$ that is less than the stroke C.

In an advantageous disposition as explained below, the unit 14 is made in such a manner as to further comprises a septum 33 or self-sealing pierceable diaphragm that is accessible from one of its faces and that provides access, e.g. to the needle of a syringe, directly into the second branch 17.

The unit 14 and the bag 12 are designed to be implanted subcutaneously, e.g. close behind the skin P of a patient, and in any event at a distance D that allows the ferromagnetic head 28 to be influenced by an induction coil 34 capable of delivering a magnetic field of sufficient power to overcome the opposing action of the resilient member 30.

The above-described apparatus enables the following method to be implemented.

Once the prosthesis has been implanted, and regardless of its intended purpose, it should be understood that the inflatable envelope 1a, 1b, or 1c is in its state of minimum expansion and that the liquid needed to inflate it occupies the tank 13 and the circuit 15, and possibly also the tube 11.

Initial operation consists in applying deformation pressure to the bag 12 by manual action through the skin P so as to cause the liquid to be transferred and put under pressure both in the bag 12 and in the first branch 16 so that the liquid penetrates into the well 26 via the tube 19.

The arrival of this liquid under pressure puts additional stress on the spring 30 so that the sensing member as constituted by the diaphragm and its nipple is subjected to displacement in the direction of arrow $f_1$, thereby increasing the volume of the chamber 22.

Figure 5:
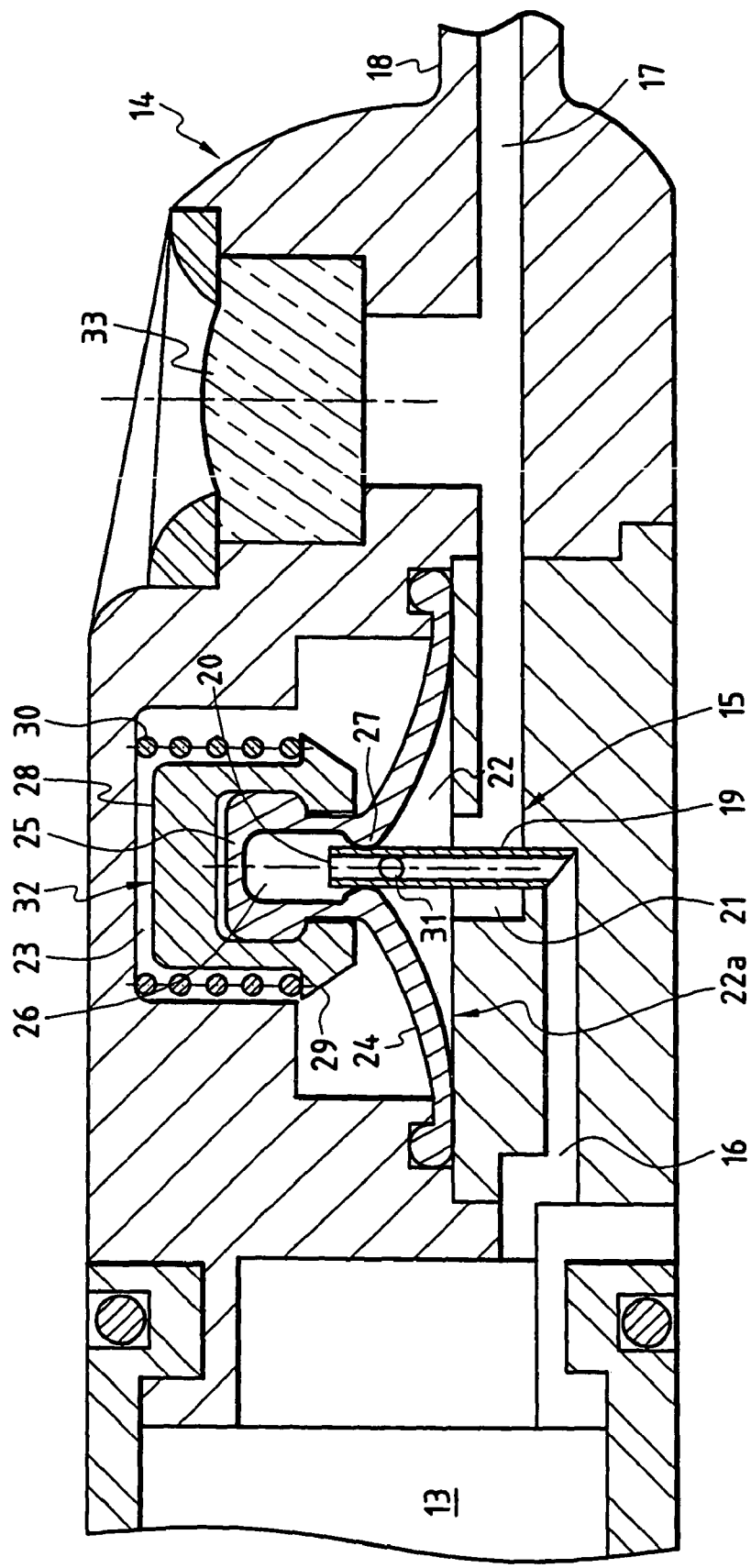

A first consequence of this is to open the prechamber 21, and a second consequence is to cause the diaphragm 24 to slide over the tube 19 until the sealing ring 27 uncovers the radial hole 31, as shown in FIG. 5.

An examination of this figure reveals that the first branch 16 communicates via the hole 31 with the chamber 22 which is put into communication with the prechamber 21 into which the second branch 17 opens.

By the above-described means, the quantity of liquid contained in the tank 13 is transferred into the inflatable envelope 1a, 1b, or 1c until it is maximally inflated.

After it has been inflated, ceasing to act on the bag 12 causes pressure to be balanced in the circuit 15 so that the spring 30 returns the check valve to its closed position as shown in FIG. 3 or FIG. 4, in which the diaphragm 24 isolates the prechamber 21 from the chamber 22 and the gasket isolates the prechamber 21 from the hole 31 so as to interrupt any communication between the branches 16 and 17.

In an on/off type of application, such as an application to the envelope 1b or 1c, for example, the situation as acquired in this manner is maintained until the need arises to cause the envelope 1b or 1c to be deflated.

Under such circumstances, the coil 34 is placed over the ferromagnetic head 30 so as to deliver a field which exerts an attractive force overcoming the opposing action of the return spring 30. From the position shown in FIG. 4, the sensing member is raised in the direction of arrow $f_1$ until the diaphragm 24 puts the chamber 22 and the prechamber 21 into communication, and thereafter uncovers the hole 31 which reestablishes communication between the branch 17 and the branch 16.

The return of liquid from the envelope to the tank can then take place either naturally due to the pressure exerted by the surrounding tissue on the envelope, or else because of the shape memory of the bag 12 which tends to return to its initial position, thereby encouraging return of the liquid, or indeed by a combination of both effects.

In the particular application of the prosthesis to a gastric implant, the second stage of adjustment then consists in using successive pulses to power the coil 34 so as to act on the sensing member of the check valve constituted by the assembly 24, 25, and 28 so as to readmit small quantities of liquid returning to the tank 13, thereby progressively deflating the gastric implant until the section or striction that it is to produce has been reached.

The means described above in terms of structure and function solve the problems mentioned in the introduction and make it possible in particular for the practitioner in charge of monitoring proper operation of a gastric ring to cause the check valve or sensing member to open while the practitioner remains in a position that is remote, e.g. because a power supply line 35 for the coil 34 and including a switch 36 is made available to the practitioner outside the zone(s) occupied by the patient, and in which the practitioner would run the risk of being exposed to the radiation produced by the technical means used for viewing by radiography or radioscopy or the like.

In addition to the advantages obtained by such apparatus, it should be observed that it provides a maximum amount of safety in the interests of the patient in the event of faulty operation or uncontrolled blocking of the sensing member constituting the check valve.

Supposing that the check valve becomes inoperative, defective, or incapable of performing the opening and closing function that is required of it, the practitioner can still act manually and directly to admit or remove a portion of the liquid by acting on a syringe whose needle is caused to puncture the septum 33, thereby gaining direct access to the second branch 17 and thus to the tube 11 leading to the inside volume of the inflatable envelope where a quantity of liquid can be added or removed as a function of requirements.

The invention claimed is:

1. A method of controlling inflation of an inflatable prosthetic envelope by connecting the envelope to a transfer tube and placing said tube into communication with a bag from which a liquid can be caused to flow to cause said envelope either to inflate or to deflate, the method comprising the steps of:

confining in said bag, which is deformable, a quantity of liquid that is not less than the capacity of the envelope;

interposing, between said bag and the envelope, a non-return check valve comprising a moving member for opening and closing the transfer circuit, a resilient return member urging the moving member into a closed position, and a ferromagnetic sensing element attached to the moving member;

manually applying deformation pressure to the bag to transfer a quantity of liquid from the bag so as to inflate the envelope;

selectively applying a magnetic field adjacent the check valve, thereby remotely causing the check valve to open to allow liquid that has been admitted into the envelope to return to the bag in order to deflate the envelope until the envelope reaches the desired volume; and removing or interrupting the magnetic field, thereby releasing the sensing member and allowing the moving member to be urged back into the closed position by the resilient member in the absence of an external magnetic field.

2. A method according to claim 1, wherein the magnetic field is applied from outside the epidermis.

3. Apparatus for controlling the inflation of an inflatable prosthetic envelope, the apparatus comprising a deformable bag containing a supply of liquid suitable for inflating said envelope by flowing in a transfer circuit under the control of a controllable shutter, wherein:
the bag is connected to a unit defining a transfer circuit under the control of the shutter and connected to the envelope; and the shutter comprises a non-return check valve comprising:
a moving member for opening and closing the transfer circuit,
a resilient return member urging the moving member into a closed position, and
a ferromagnetic sensing member attached to the moving member for opening the moving member when an external magnetic field is applied, with the resilient return member urging the moving member into the closed position when no magnetic field is applied.

4. Apparatus according to claim 3, wherein the check valve is placed in the unit which further includes, in a portion of the transfer circuit between said check valve and the envelope, a pierceable and closable septum or diaphragm.

5. Apparatus according to claim 3, wherein the unit is directly associated with the bag.

6. Apparatus according to claim 3, wherein the bag is elastically deformable and possesses shape memory concerning its maximum retention capacity.

7. Apparatus according to claim 3, wherein the check valve is placed in the transfer circuit defined by the unit, which circuit comprises a first branch in communication with the bag, an intercommunication tube for communication between the first branch and a chamber, a second branch suitable for being placed in communication with the chamber, and inside the chamber the moving member of the check valve which is mounted to slide on the tube to open or close communication with the second branch.

8. Apparatus according to claim 7, wherein the intercommunication tube projects into the chamber which is defined by an elastically deformable diaphragm and which forms a sealing lip surrounding a well and engaged on the tube which opens out into the well via its open end and which possesses at least one radial hole for entering into communication with the chamber.

9. Apparatus according to claim 8, wherein the well is defined by a nipple presented by the diaphragm and which is in turn covered by a ferromagnetic head associated with a resilient member urging the diaphragm continuously towards a position in which the radial hole in the tube is closed and communication between the first and second branches is interrupted.

10. Apparatus according to claim 9, wherein the head is placed in a closed cavity defined by the unit and separated from the chamber by the diaphragm.

11. Apparatus according to claim 8, wherein the head forms a shoulder against which a helical spring bears, the spring operating in compression and being put in the cavity under prestress.

12. Apparatus according to claim 8, wherein the tube presents a height H measured from a bearing plane presented by the chamber and against which the diaphragm presses when the second branch is closed, said height H being greater than stroke C of the check valve.

13. Apparatus according to claim 8, wherein the tube presents at least one radial hole which is situated at a height h from the bearing plane that is less than the stroke C of the check valve.

14. An implantable prosthesis comprising an inflatable envelope and inflatable control apparatus according to claim 3.

* * * * *